(12) United States Patent
Hudgins et al.

(10) Patent No.: US 8,672,973 B2
(45) Date of Patent: Mar. 18, 2014

(54) FACET REPLACEMENT/SPACING AND FLEXIBLE SPINAL STABILIZATION

(75) Inventors: Robert Garryl Hudgins, Burnsville, MN (US); Michael E. Lancial, St. Louis Park, MN (US); Hugh D. Hestad, Edina, MN (US)

(73) Assignee: Zimmer Spine Inc., Minneapolis, MN (US)

( * ) Notice: Subject to any disclaimer, the term of this patent is extended or adjusted under 35 U.S.C. 154(b) by 154 days.

(21) Appl. No.: 13/207,970

(22) Filed: Aug. 11, 2011

(65) Prior Publication Data

US 2011/0295323 A1 Dec. 1, 2011

Related U.S. Application Data

(63) Continuation of application No. 11/221,938, filed on Sep. 8, 2005, now abandoned.

(51) Int. Cl.
*A61B 17/70* (2006.01)

(52) U.S. Cl.
USPC ........................................ 606/247; 623/17.11

(58) Field of Classification Search
USPC ......... 623/17.11–17.16; 606/53, 60, 246, 247
See application file for complete search history.

(56) References Cited

U.S. PATENT DOCUMENTS

| | | | | |
|---|---|---|---|---|
| 3,867,728 A | * | 2/1975 | Stubstad et al. | 623/17.16 |
| 4,634,720 A | * | 1/1987 | Dorman et al. | 521/63 |
| 4,743,260 A | | 5/1988 | Burton | |
| 4,778,469 A | * | 10/1988 | Lin et al. | 128/898 |
| 4,902,297 A | * | 2/1990 | Devanathan | 623/23.51 |
| 4,938,778 A | * | 7/1990 | Ohyabu et al. | 427/245 |
| 4,955,911 A | * | 9/1990 | Frey et al. | 623/23.51 |
| 4,978,355 A | * | 12/1990 | Frey et al. | 623/23.54 |
| 5,011,497 A | | 4/1991 | Persson et al. | |
| 5,071,437 A | * | 12/1991 | Steffee | 623/17.16 |
| 5,219,363 A | * | 6/1993 | Crowninshield et al. | 623/23.34 |
| 5,232,878 A | * | 8/1993 | Kasuga et al. | 501/10 |
| 5,236,457 A | * | 8/1993 | Devanathan | 128/898 |

(Continued)

FOREIGN PATENT DOCUMENTS

EP 392076 A1 10/1990
EP 356112 B1 12/1993

(Continued)

OTHER PUBLICATIONS

International Search Report and Written Opinion, Aug. 8, 2007, 7 pgs.

*Primary Examiner* — Pedro Philogene
*Assistant Examiner* — Lynnsy Schneider
(74) *Attorney, Agent, or Firm* — Seager Tufte & Wickhem LLC

(57) ABSTRACT

Spinal stabilization devices for addressing back pain originating in the facet joints and the spinous processes of the vertebrae. One embodiment of the present invention includes a substantially T-shaped facet implant for insertion between the facets of two successive vertebrae after a desired amount of the articulating surfaces have been resected. The long and flat portion of the T-shaped facet implant is inserted in between the facets and then the wings of the T-shape, also called fixation tabs, are secured to the spine to secure the facet implant into place. The T-shape implant may also be a part of a spinal stabilization system that includes a facet implant, a spinous process spacer, and a flexible connecting member securing the same.

2 Claims, 16 Drawing Sheets

(56) References Cited

U.S. PATENT DOCUMENTS

| | | | |
|---|---|---|---|
| 5,282,861 A * | 2/1994 | Kaplan | 623/23.51 |
| 5,375,823 A | 12/1994 | Navas | |
| 5,443,512 A * | 8/1995 | Parr et al. | 623/23.51 |
| 5,443,515 A | 8/1995 | Cohen | |
| 5,458,643 A * | 10/1995 | Oka et al. | 623/17.16 |
| 5,524,695 A * | 6/1996 | Schwartz | 164/34 |
| 5,540,688 A | 7/1996 | Navas | |
| 5,545,229 A * | 8/1996 | Parsons et al. | 623/17.15 |
| 5,571,187 A * | 11/1996 | Devanathan | 623/66.1 |
| 5,897,592 A * | 4/1999 | Caldarise et al. | 128/898 |
| 6,063,442 A * | 5/2000 | Cohen et al. | 427/250 |
| 6,258,125 B1 | 7/2001 | Paul et al. | |
| 6,554,863 B2 | 4/2003 | Paul et al. | |
| 6,565,605 B2 | 5/2003 | Goble et al. | |
| 6,569,201 B2 * | 5/2003 | Moumene et al. | 623/17.11 |
| 6,579,319 B2 | 6/2003 | Goble et al. | |
| 6,610,091 B1 | 8/2003 | Reiley | |
| 6,626,950 B2 * | 9/2003 | Brown et al. | 623/23.72 |
| 6,669,732 B2 * | 12/2003 | Serhan et al. | 623/17.16 |
| 6,673,075 B2 * | 1/2004 | Santilli | 623/17.16 |
| 6,726,720 B2 | 4/2004 | Ross et al. | |
| 6,740,186 B2 * | 5/2004 | Hawkins et al. | 156/242 |
| 7,169,181 B2 * | 1/2007 | Kuras | 623/17.11 |
| 7,192,447 B2 | 3/2007 | Rhoda | |
| 7,449,194 B2 * | 11/2008 | Lelah et al. | 424/404 |
| 7,468,075 B2 * | 12/2008 | Lang et al. | 623/16.11 |
| 7,744,630 B2 * | 6/2010 | Lancial | 606/247 |
| 7,842,096 B2 * | 11/2010 | Fridshtand et al. | 623/23.35 |
| 7,879,100 B2 * | 2/2011 | Denoziere et al. | 623/17.11 |
| 7,918,382 B2 * | 4/2011 | Charlebois et al. | 228/248.1 |
| 7,922,766 B2 * | 4/2011 | Grob et al. | 623/17.11 |
| 7,998,172 B2 * | 8/2011 | Blain | 606/247 |
| 8,021,424 B2 * | 9/2011 | Beger et al. | 623/17.11 |
| 8,029,540 B2 * | 10/2011 | Winslow et al. | 606/247 |
| 8,048,116 B2 * | 11/2011 | Lee | 606/247 |
| 8,052,728 B2 * | 11/2011 | Hestad | 606/279 |
| 8,070,782 B2 * | 12/2011 | McKay | 606/279 |
| 8,172,877 B2 * | 5/2012 | Winslow et al. | 606/247 |
| 8,191,760 B2 * | 6/2012 | Charlebois et al. | 228/248.1 |
| 8,303,879 B2 * | 11/2012 | Bertele et al. | 264/273 |
| 8,361,150 B2 * | 1/2013 | Zhang et al. | 623/17.11 |
| 2001/0016773 A1 | 8/2001 | Serhan et al. | |
| 2002/0161366 A1 | 10/2002 | Robie et al. | |
| 2004/0186472 A1 | 9/2004 | Lewis | |
| 2004/0210310 A1 | 10/2004 | Trieu | |
| 2004/0210314 A1 * | 10/2004 | Michelson | 623/17.16 |
| 2005/0100578 A1 | 5/2005 | Schmid et al. | |
| 2005/0131538 A1 * | 6/2005 | Chervitz et al. | 623/17.11 |
| 2005/0159814 A1 | 7/2005 | Karahalios | |
| 2006/0111781 A1 | 5/2006 | Petersen | |
| 2006/0121084 A1 | 6/2006 | Borden et al. | |
| 2006/0178749 A1 | 8/2006 | Pendleton et al. | |
| 2006/0241759 A1 * | 10/2006 | Trieu | 623/17.11 |
| 2007/0088437 A1 * | 4/2007 | Betz et al. | 623/17.11 |
| 2007/0093912 A1 * | 4/2007 | Borden | 623/23.75 |
| 2007/0135814 A1 * | 6/2007 | Farris | 606/61 |
| 2007/0179622 A1 * | 8/2007 | Denoziere et al. | 623/17.16 |
| 2007/0185492 A1 | 8/2007 | Chervitz et al. | |
| 2007/0233272 A1 * | 10/2007 | Boyce et al. | 623/23.63 |
| 2007/0255412 A1 * | 11/2007 | Hajaj et al. | 623/17.11 |
| 2007/0270967 A1 | 11/2007 | Fallin et al. | |
| 2008/0161927 A1 * | 7/2008 | Savage et al. | 623/17.16 |
| 2008/0288077 A1 * | 11/2008 | Reo et al. | 623/17.16 |
| 2008/0306609 A1 * | 12/2008 | Lee et al. | 623/23.58 |
| 2009/0030521 A1 * | 1/2009 | Lee et al. | 623/17.16 |
| 2009/0036986 A1 * | 2/2009 | Lancial et al. | 623/17.11 |
| 2009/0326657 A1 * | 12/2009 | Grinberg et al. | 623/17.16 |
| 2010/0094426 A1 * | 4/2010 | Grohowski et al. | 623/17.16 |
| 2010/0137990 A1 * | 6/2010 | Apatsidis et al. | 623/17.16 |
| 2010/0268227 A1 * | 10/2010 | Tong et al. | 606/60 |
| 2011/0060366 A1 * | 3/2011 | Heim et al. | 606/247 |
| 2011/0093076 A1 * | 4/2011 | Reo et al. | 623/17.16 |
| 2012/0221049 A1 * | 8/2012 | Blain | 606/247 |

FOREIGN PATENT DOCUMENTS

| | | |
|---|---|---|
| EP | 669109 B1 | 5/1999 |
| WO | 8903663 A1 | 5/1989 |
| WO | 9417745 A1 | 8/1994 |
| WO | 2005047467 A3 | 8/2005 |
| WO | 2006078662 A1 | 7/2006 |
| WO | 2007123861 A3 | 8/2008 |
| WO | 2008034276 A3 | 10/2008 |

* cited by examiner

FACET REPLACEMENT/SPACING AND FLEXIBLE SPINAL STABILIZATION

CROSS-REFERENCE TO RELATED APPLICATIONS

This application is a continuation of U.S. application Ser. No. 11/221,938 filed on Sep. 8, 2005, which is incorporated by reference herein in its entirety.

TECHNICAL FIELD

The present invention is related to spinal stabilization devices. More particularly, the present invention relates to devices and systems for addressing back pain originating in the vertebrae by adding devices for the flexible stabilization of the facet joints and adjacent spinous processes.

BACKGROUND

The spinal column is a highly complex system of bones and connective tissues that provides support for the body and protects the delicate spinal flexible connecting member and nerves. The spinal column includes a series of vertebrae stacked one on top of the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal flexible connecting member and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal pathologies may threaten the critical elements of the nervous system housed within the spinal column.

A variety of systems and surgical procedures have been disclosed in the art to alleviate the symptoms of these and other spinal pathologies. One of the most common surgical procedures today is arthrodesis, or spine fusion, of one or more spine segments. Spine fusion is used to treat many spinal disorders, including kyphosis, spondylolisthesis, and lordosis. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused motion segments. Also, the fusion device, whether artificial or biological, may migrate out of the fusion site.

Instead of fusing sections of the spine, various different devices have been implanted into the spine to stabilize the spine without completely restricting movement. These flexible spinal stabilization methods may not result in complete spinal fusion. Some systems include implanting artificial assemblies in or on the spinal column. These assemblies may be classified as anterior, posterior, or lateral implants. Implants may also be attached by screws or attachment members inserted through the pedicles. One posterior stabilization method includes spinal immobilization utilizing pedicle screws and wire. Other spinal systems may include a variety of other procedures and apparatuses for attending spinal problems and pain. However, there is a continual need for alternative systems and devices for stabilization of the spine.

SUMMARY

The present invention includes a spinal stabilization device that distracts the vertebral bodies at the spinous process or across the facet joint to eliminate pain associated with spinal stenosis, facet arthropathy, spondylolisthesis, and other spinal column disorders.

One embodiment of the present invention includes a facet implant for the stabilization of a facet joint between two adjacent vertebrae, the facet implant may include a "T-shaped" body with a bearing body and fixation wings, the bearing body inserted between the opposing facets and the fixation wings utilized to secure the facet implant to the spine.

Another embodiment of the present invention includes a spinal stabilization device comprising a facet implant, a spinous process spacer, a flexible connecting member, and anchoring elements, the facet implant inserted between the opposing facets of two successive vertebrae, the spinous process spacer inserted between the spinous processes of the two adjacent vertebrae, the flexible connecting member linking the facet implant and the spinous process spacer and the anchoring elements anchoring the flexible connecting member to the spine.

Another embodiment is a prosthesis for the stabilization of a diseased or traumatized facet of a vertebra including a facet implant member having an articulating surface for insertion between two opposing facets of two adjacent vertebrae, the articulating surface providing support for the two opposing facets and support between the two opposing facets, and two fixation tabs attached to the articulating surface wherein the facet implant member and the two fixation tabs form a substantially T-shape.

Another embodiment of the invention may include a facet implant for securing the opposing facets of two vertebrae, the facet implant including a band for securing to the two vertebrae, the band including a means for securing the band to the two vertebrae, the band providing a restraining force between the two vertebrae to restrict the relative movement of the two vertebrae.

Yet another embodiment of the present invention may include a method for stabilizing two adjacent vertebrae having opposing facets including the steps of resecting at least one of the two opposing facets a desired amount, positioning a facet implant between the two opposing facets, and connecting the facet implant to at least one of the two adjacent vertebrae so that the facet implant provides structural support to at least one of the opposing facets.

Another aspect of the invention includes a method for stabilizing a spine having adjacent vertebrae that have opposing facets comprising inserting a facet implant including a facet bearing body, the facet bearing body providing at least one of spacing and support to at least one of the two opposing facets, placing a spinous process spacer for placement between the spinous processes of the first and second adjacent vertebrae, securing a flexible connecting member between the spinous process spacer and the first vertebrae, and affixing the flexible connecting member to the spine with a bone anchoring fastener.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention includes multiple apparatuses and methods for spinal stabilization. The use of the term "stabilization" in the present description refers to securing adjacent vertebrae such that the movement between them is limited to a desired amount. During this stabilization the function of the spine to support the skeleton and to protect the spinal flexible connecting member is preserved. Stabilization may also be achieved by not reducing movement but by simply providing increased structural integrity between adjacent vertebrae. Various spinal stabilization devices will first be discussed that can be individually utilized for stabilization and then the incorporation of the devices into a system will be shown.

Figure 4:
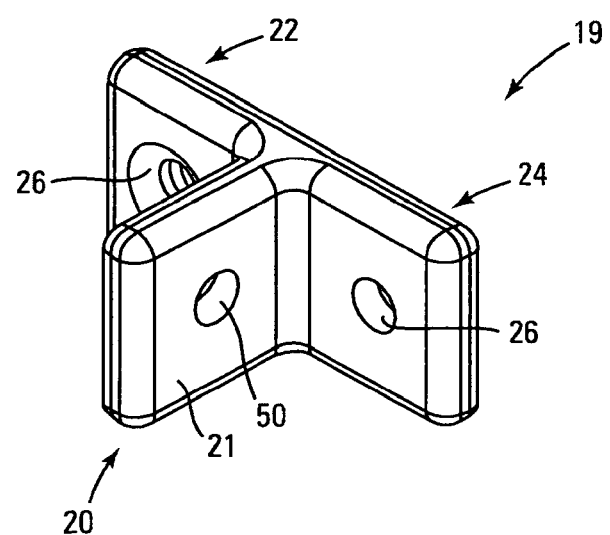
FIG. 4 illustrates a perspective view of one embodiment of a facet implant of the present invention.

A facet implant 19 of the present invention is illustrated in FIG. 4. The facet implant 19 is a prosthesis for the augmentation, stabilization, and/or replacement of a diseased, traumatized, or otherwise compromised facet of a mammalian vertebra. The facet implant 19 may provide joint spacing, joint stabilization, joint capsule replacement, and/or an articulating surface for an opposing pair of facets to a facet joint. One embodiment of the facet implant 19 may include a bearing body 20 (a facet bearing body) having a facet bearing surface 21, a first fixation wing 22, and a second fixation wing 24. The bearing body 20 may also be known as an articulating body or a facet bearing means. Likewise, the facet bearing surface 21 may also be known as an articulating surface and the fixation wings 22 and 24 may be known as fixation means or fixation tabs. Other terms may also be utilized to describe these portions of the facet implant 19 without changing the nature of the invention.

The bearing body 20 of the facet implant 19 may be attached to or integrally formed with the fixation wings 22 and 24 such that the bearing body 20 extends in a generally perpendicular direction from the plane created by fixation wings 22 and 24. The fixation wings 22 and 24 may further include holes 26. Each hole 26 may accept an attachment member 25 for attaching the facet implant 19 to the spine in the desired position. The fixation wings 22 and 24 may be rigidly attached to the bearing body 20. However, in alternative embodiments, the bearing body 20 and fixation wings 22 and 24 may be attached to vertebrae in a deformable manner such that the bearing body 20 and/or fixation wings 22 and 24 can be bent, twisted, formed, shaped, or generally positioned relative to each other and/or relative to the vertebrae. The bearing body 20 and fixation wings 22 and 24 can themselves be deformable as well. Moreover, the bearing body 20 and fixation wings 22 and 24 can be made of one piece or more than one piece of material, including, but not limited to, materials that are layered, woven, stitched, or otherwise joined with other materials. The facet bearing surface 21 is present on each side of bearing body 20.

Making the facet implant 19 with substantially flexible materials may allow for the joints to move freely after implantation. Making the facet implant 19 with stiffer materials may increasingly restrict the movement of the opposing facets. In other words, using polymers with a high modulus of elasticity or a low modulus of elasticity may change the amount the spine is restricted from moving. One such modulus range may be from approximately 0.5 megapascals to 3 megapascals. Depending on the requirements of each insertion, a variety of material and material combinations may be incorporated.

In one embodiment, the facet implant 19, bearing body 20, and the fixation wings 22 and 24 may be made of a polymeric elastomer material. In further embodiments, the facet bearing body 20 and the fixation wings 22 and 24 may be made of other materials, such as, but not limited to, polyurethane, fluoropolymers, PEEK (polyetheretherketone), Ultra-PEEK, polycarbonate based polyurethane elastomer, etc. The bearing body 20 and bearing surface 21 may be preferably made of a polymer material that mimics the body's natural facet joints, such as ultra high molecular weight polyethylene or some other polymer, such as, for example, hydrogel. The polymer selected may be lubricious, low friction, abrasion resistant, and biocompatible. The polymer selected may also include certain lubricious properties.

The bearing body 20 and fixation wings 22 and 24 may be made entirely of a desired elastomer material or may include a combination of materials that may be integrated in any manner desired to achieve a desired result. Desired results may include different structural characteristics and/or different surface characteristics. Additional embodiments may include a first core material coated by a second surface material.

Attachment members 25 may be any type of appropriate biomedical attachment member 25 or may be replaced with any type of bone attachment anchors, screws, bone fasteners, bone attachment means, or any other fixation means for securing the facet implant 19 in the selected position. When the attachment member 25 is a screw, for example, the screw type and length may be selected depending on the screw's insertion point. Moreover, the angle of insertion of the attachment members 25 may be selected to accommodate the desired attachment member 25. In still further embodiments, the facet implant 19 may also be secured to the bone surface using a biomedical adhesive in addition to, or in alternative to, attachment member 25. Another fixation means may include a post cemented into a cavity created in the bone. Such an implant may be similar to a dental post or a hip stem.

Figure 7:
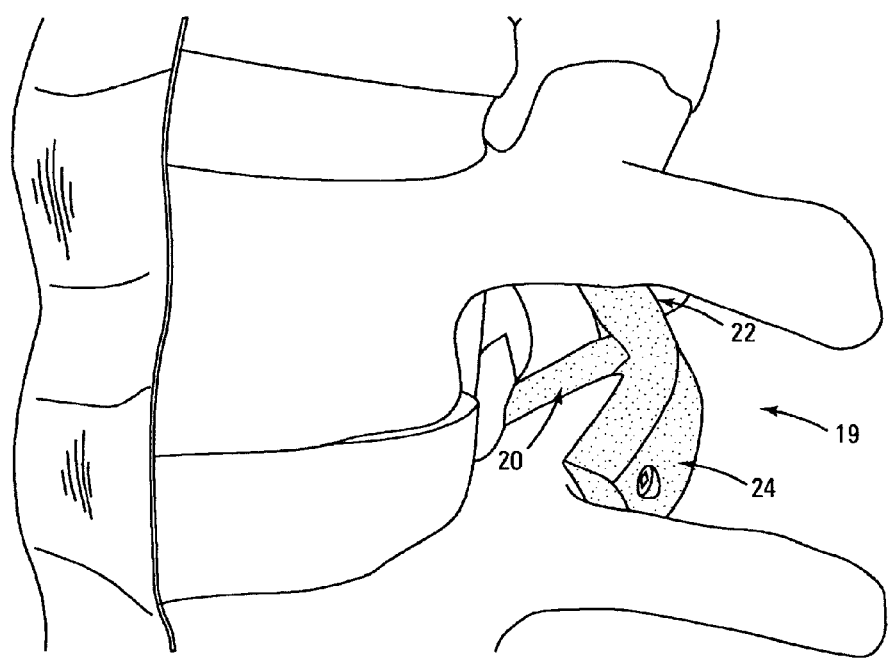
FIG. 7 illustrates the facet implant of FIG. 4 inserted into the spine.

The facet implant 19 may be inserted by first opening a surgical site around the facet joint in any manner desired. The lateral joint capsule may then be cut. The medial side of the capsule also may be cut to eliminate a possible pain source. Alternatively, the lateral and medial capsule may be left intact to provide improved stability. The faces of the facet joints to be stabilized may then be resected a desired amount. In some embodiments, and depending on the particular shape of the facet implant 19, the facets may not be resected at all. The bearing body 20 with the facet bearing surface 21 may then be inserted between the opposing faces of the facet joint. As illustrated in FIG. 7, one insertion position may include positioning the fixation wings 22 and 24 on the superior and inferior vertebrae with the bearing body 20 secured between the opposing facets. Finally, the facet implant 19 is secured in place by attaching the fixation wings 22 and 24 utilizing one or more attachment members 25 through holes 26.

The attachment member 25 for the superior vertebra may be targeted to go through the resected bone surface, i.e., the remaining portion of the facet, and into the lamina. The attachment member 25 for the inferior vertebra may go through some portion of a resected bone surface and into the pedicle. As may be appreciated, depending on the size of the implant 19, the size of the fixation wings 22 and 24, the amount of resected bone, and the length of the attachment members 25, a variety of facet implant 19 positions and attachment member paths may be selected by one of skill in the art to achieve the intended results. Moreover, as discussed further herein, various alternative embodiments of the facet implant 19 may be more useful depending on the amount of the facet joint removed during the insertion process. The bearing body 20 and the facet bearing surface 21 of the facet implant 19 may provide spacing, support, and/or an articulating surface to the opposing facets of the facet joint. The fixation wings 22 and 24 may be bent and deformed to adapt to the contours of each vertebra and to insure the correct positioning of the bearing body 20. Greater or lesser amounts of force may be exerted on the vertebrae depending on the desired results.

Figure 6:
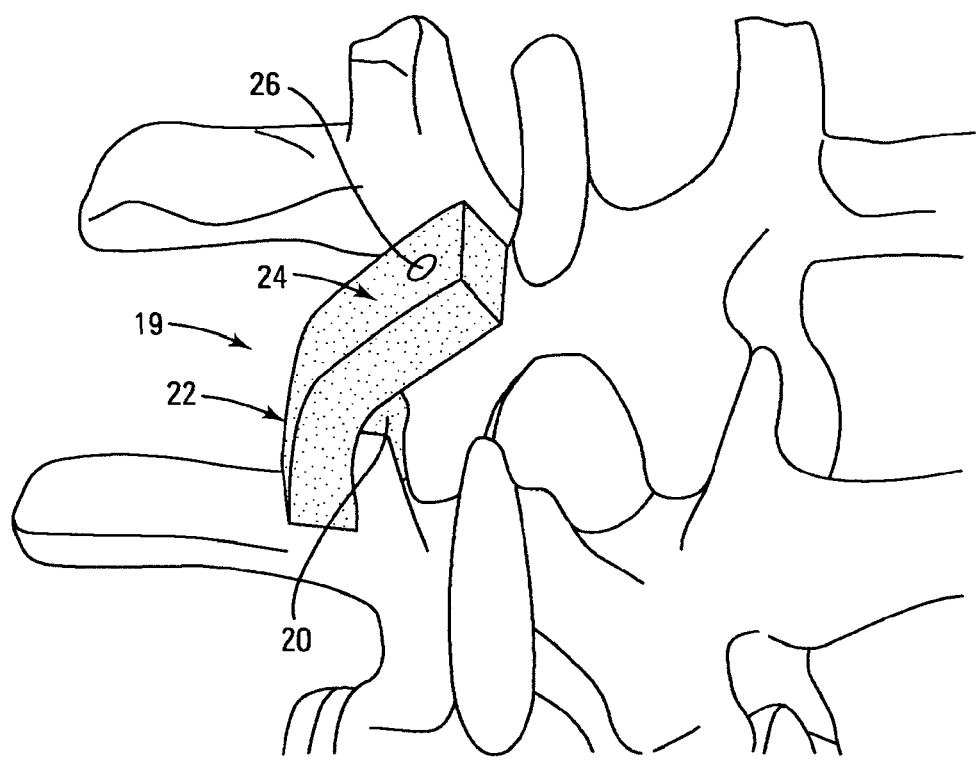
FIG. 6 illustrates another alternative embodiment of the facet implant of FIG. 4 inserted into the spine.

As illustrated in FIGS. 6-7, the fixation tabs 22 and 24 of facet implant 19 may be bent, stretched, or otherwise deformed from their initially planar orientation to conform with each vertebra. The fixation wings 22 and 24 help to stabilize the relative positions of the opposing facet surfaces around the bearing body 20 by exerting a restraining force on the vertebrae. The restraining force may hold the facet surfaces in a desired orientation and may prevent the facet joint from moving out of a desired orientation. The force exerted by the fixation wings 22 and 24 on the two successive vertebrae depend on the material utilized to construct the facet implant 19 and how and where the fixation wings 22 and 24 are secured to the bone. The "T" shaped structure of the facet implant 19 may be twisted and stretched as desired in order to exert force in the desired manner to achieve the desired stabilization. For example, the fixation wings 22 and 24 may be "stretched" out before being secured, resulting in an increased restraining or compressive force acting on the facet joint and facet surfaces. Insertion of the facet implant 19 and the final position of the same may therefore be highly customizable. In alternative embodiments, one or two or more fixation wings 22, 24 may be utilized to form the facet implant 19.

Figure 5:
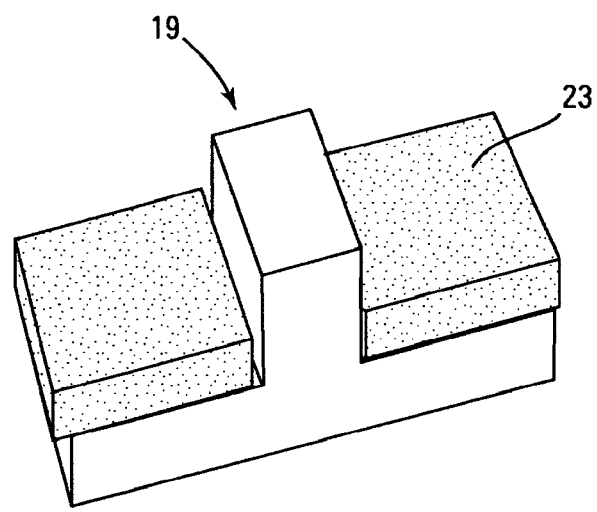
FIG. 5 illustrates an alternative embodiment of the facet implant of FIG. 4.

As illustrated in FIG. 5, in one alternative embodiment of facet implant 19 the facet implant may include a bone in-growth inducing material 23. Bone in-growth inducing material 23 may include placing a porous bone growth material, such as tantalum metal, on a selected portion of the fixation wings 22 and 24. The bone growth material may be utilized with the facet implant 19 to induce bone growth around, on, or into the facet implant 19.

The tantalum metal may be tantalum vapor deposited on a vitreous carbon scaffold resulting in a highly porous structure. One example of such material may be Trabecular™ metal. Bone growth material like tantalum metal is conducive to bone formation, enabling rapid and extensive tissue infiltration that results in very strong attachment of the facet implant 19 to the bone. Moreover, tantalum metal possesses a high strength-to-weight ratio, with mechanical properties capable of withstanding physiologic stresses.

The bone in-growth materials can be incorporated into the implants during the injection molding procedures. Molds may be machined with cutouts that hold the shaped tantalum metal in place during the molding process. The bone in-growth material may then be placed into the cutouts while the mold is closed and heated. The polymer injection molding may then occur under predetermined parameters such that the polymer fills the mold and penetrates into the tantalum metal a desired amount. If the polymer viscosity is low enough so that the polymer fills the entire pore structure of the bone in-growth material, before the molding takes place the tantalum metal can be filled to a controlled depth with a material that is incompatible with the injected implant polymer. This filler material may prevent the polymer from filling the bone in-growth material in a desired pattern during the molding process. Then the filler material in the bone in-growth material can be removed by extraction with a solvent or by melting, etc.

Compression molding may be similarly used for incorporating bone in-growth material into implant 19. During compression molding the pressure for molding and penetrating the bone in-growth material may be more accurately applied and therefore obviate the need for using a filler. The compression mold may be machined with a formed cutout for the bone in-growth material. The polymer is placed into the mold, air is evacuated from the mold and polymer assembly, and pressure is applied to the polymer. Once the mold and polymer reach a desired temperature the pressure is held for a specified time. The specified time allows for polymer flow to occur as needed to both make the solid part and to allow the polymer to penetrate the bone in-growth material. If needed, however, a filler material process can be performed as previously described. Alternatively, for both injection and compression molding, the bone ingrowth material cutouts can be selectively cooled with proper mold design to help prevent undesired penetration of the polymer into the bone in-growth material.

Other bone in-growth inducing materials may include fiber metals that comprise a wire structure that forms a desired pore structure. Further materials may be coated on the facet implant to encourage bone growth, such as other porous ingrowth surfaces, hydroxyapatite, or a synthetic bone graft material. Such bone graft material may include mineralized, lyophilized collagen that can be formed into three-dimensional pads of various sizes for surgical implantation. One such material, CopiOs™ BVF, a demineralized bone matrix, available from Zimmer Spine, Edina, Minn., is a collagen sponge material used as a carrier for a bone morphogenic protein delivery medium. The CopiOs™ BVF sponge may be incorporated with the implants by making small recesses into the implants through an appropriate molding process. The small recesses allow small pieces of the sponge to be physically laid into the implants during the surgical procedure. Thus, the CopiOs™ BVF sponge can be exposed to the adjacent bone tissue and help induce bone growth on the implants.

As illustrated in FIG. 6, one alternative embodiment of facet implant 19, facet implant 19A, may not include the bearing body 20. Such a facet implant 19A may be inserted when the facets are not resected and a new articulating surface is not needed. Facet implant 19A may be affixed to the vertebrae to provide stabilization to the two successive vertebrae in a manner such as previously described.

Figure 8:
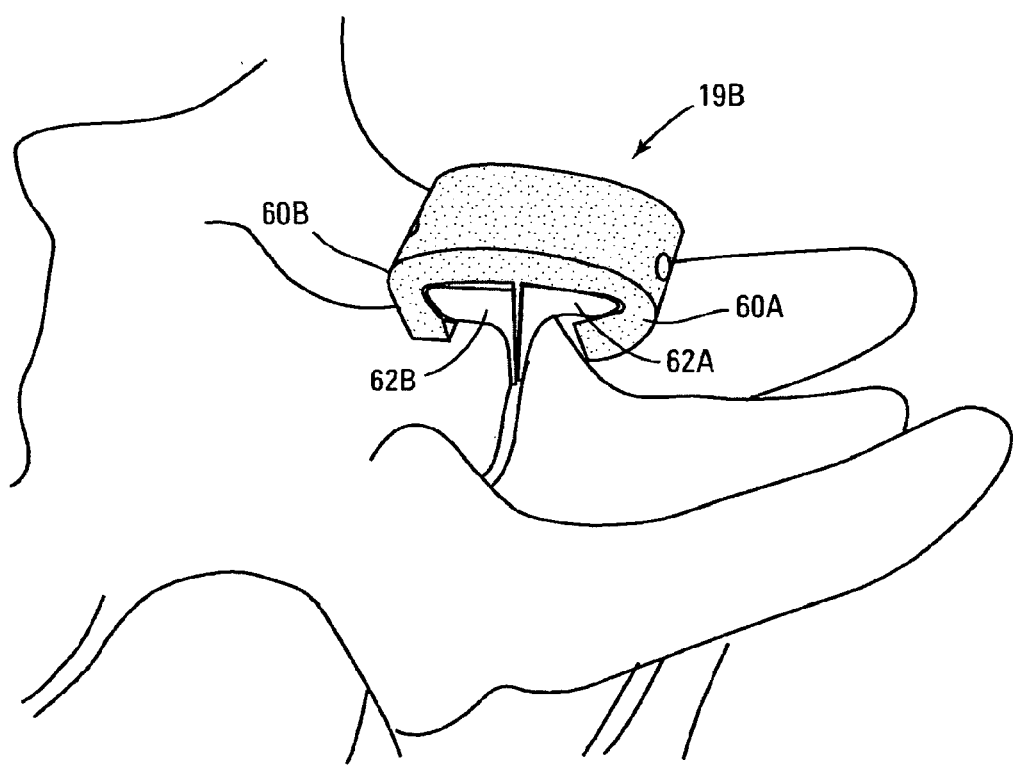
FIG. 8 illustrates another alternative embodiment of the facet implant of FIG. 4 inserted into the spine.
Figure 9:
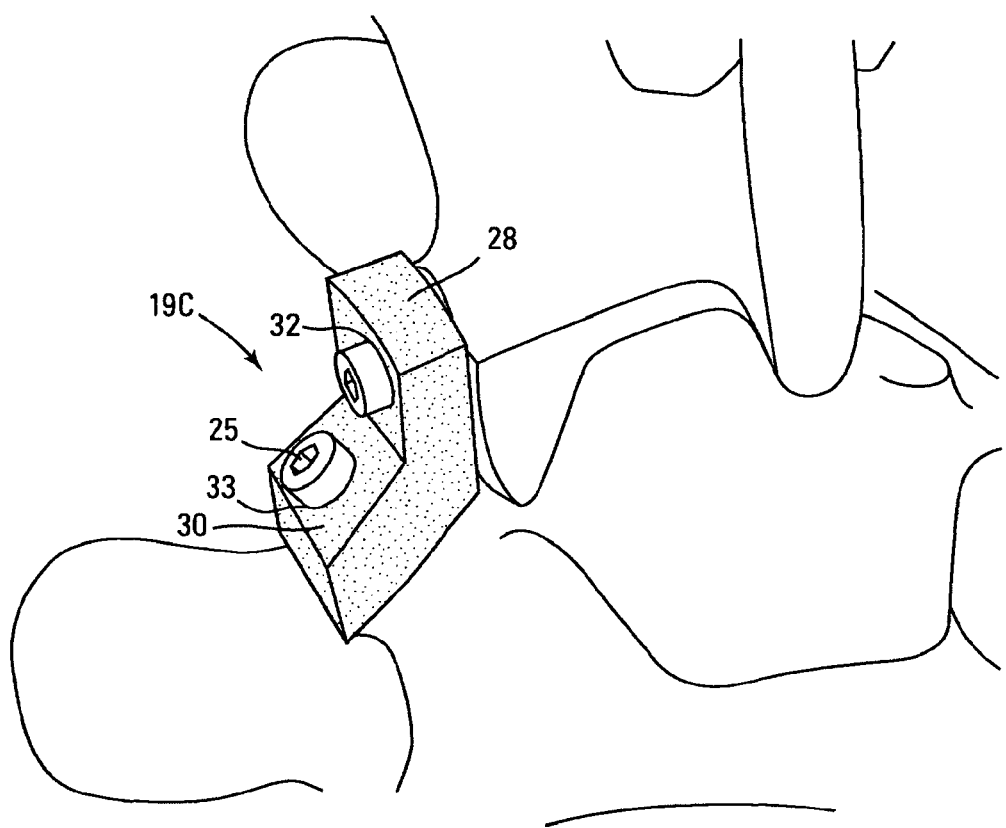
FIG. 9 illustrates another embodiment of the facet implant of FIG. 4 inserted into the spine.
Figure 10:
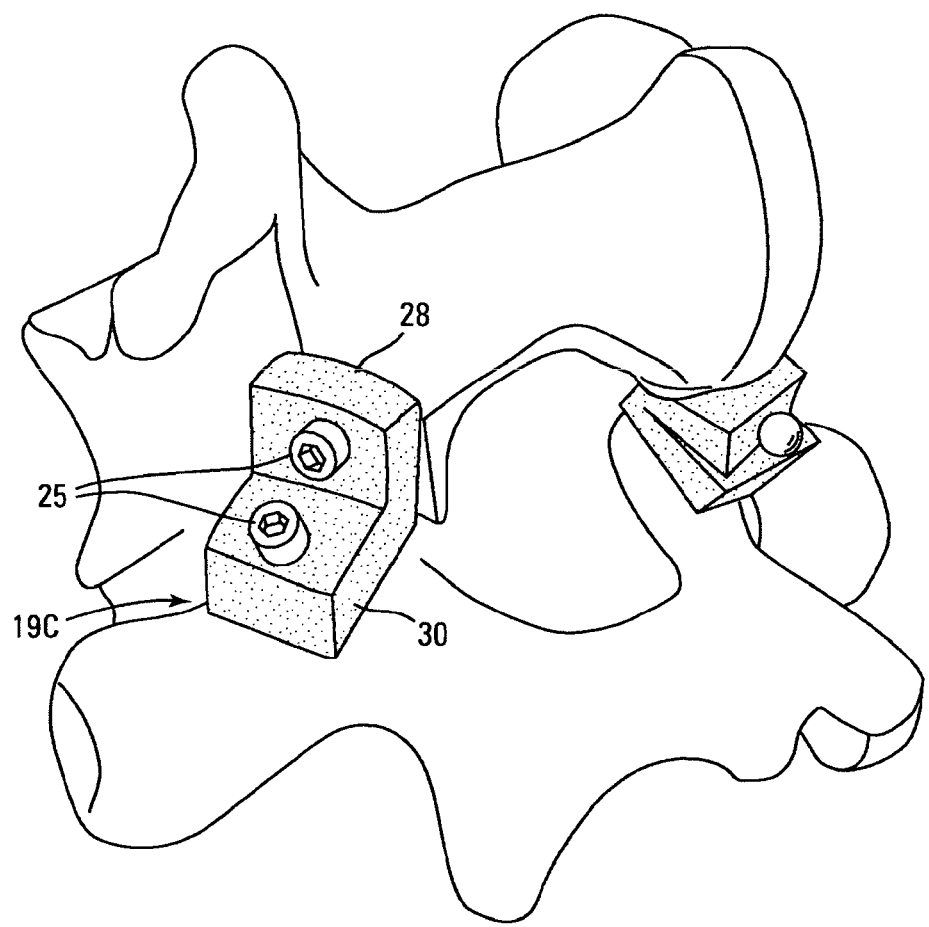
FIG. 10 illustrates another view of the facet implant of FIG. 9 inserted into the spine.
Figure 11:
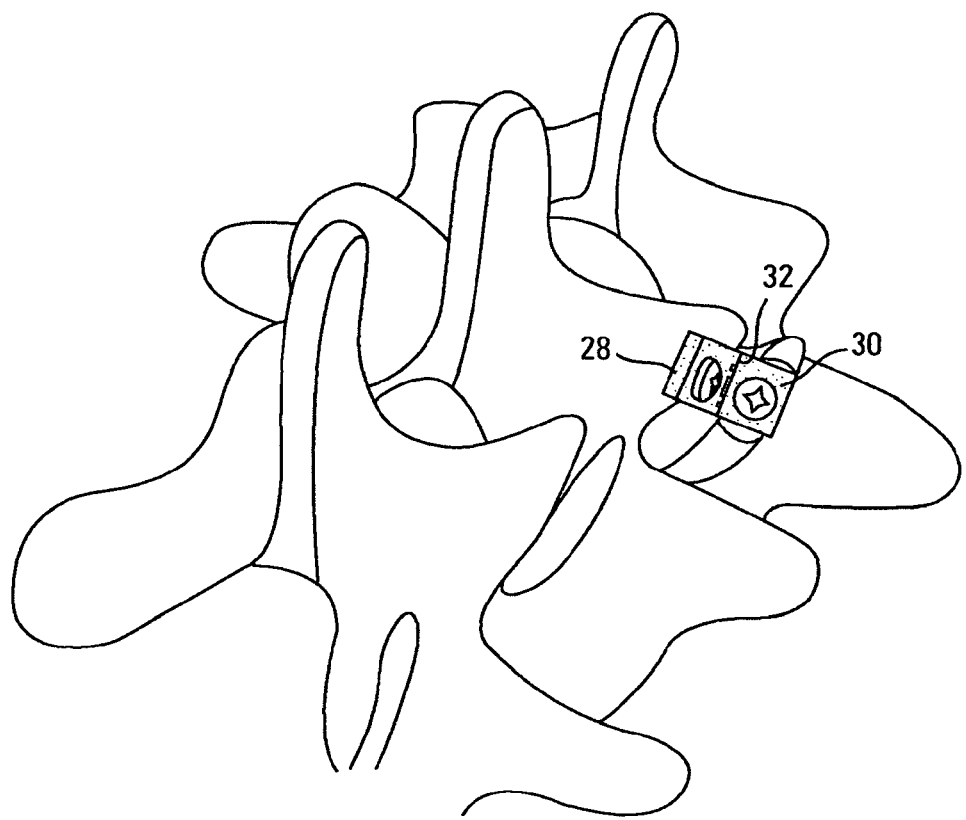
FIG. 11 illustrates another embodiment of the facet implant of FIG. 9 inserted into the spine.
Figure 12:
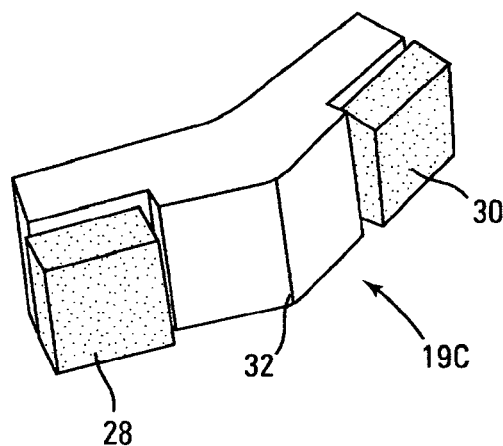
FIG. 12 illustrates an alternative embodiment of the facet implant of FIG. 9.

In another alternative embodiment of facet implant 19 illustrated in FIG. 8, facet implant 19B, the "T" shape of the facet implant 19 is retained, but may be comprised of a first body 60A and a second body 60B. Each body 60A and 60B of facet implant 19B may be a generally "L" shaped structure and include a bearing body 62A and 62B and fixation wings 64A and 64B. The bearing body 62A and 62B may further include bearing surfaces 64A and 64B.

The first and second body 60A and 60B of the facet implant 19B may be attached to the vertebrae substantially in the same manner as facet implant 19. After the first and second body 60A and 60B are affixed to the vertebrae, the band 68 may bindingly engage the first and second body 60A and 60B to each other. The elasticity of band 68 may restrain relative movement of the facets some desired amount. The bearing body 62A and bearing body 62B may position the bearing surfaces 64A and 64B in the facet joint such that the movement or rubbing in the facet joint is borne by the bearing surfaces 64A and 64B and not by the surfaces of the facets. The first and second body 60A and 60B may not be directly secured to the vertebrae and so articulation may occur between each facet surface and each corresponding body 60A and 60B. The first and second body 60A and 60B may therefore articulate relative to each other.

The band 68 may or may not be elastic like a rubber band, but may simply include some stretchy, expandable, deformable, or resilient material that allows the band 68 to provide a restraining or compressing force to the facet joint in the manner desired. Furthermore, in further embodiments, the elastic material may be compliant or non-compliant. In still further embodiments, the band 68 may be secured at a top end of the first and second body 60A and 60B of the facet implant 19B before the first and second body 60A and 60B are placed into the facet joint. The band 68 may then be secured to the vertebrae so that the facet implant 19B is retained in the desired position. The band 68 may be secured by any attachment means such as screws, adhesives etc. (not shown).

As may be appreciated, the material used to form bearing surfaces 64A and 64B and bearing body 62A and 62B of each bearing body 62A and 62B may be selected for a desired stiffness and lubricity. In addition, each bearing body 62A and 62B or a portion of each bearing surface 64A and 64B may be coated on one side with a bone growth inducing material such that over a period of time bone growth will further secure each bearing body 62A and 62B to the vertebrae.

In an alternative embodiment of facet implant 19B, each bearing body 62A and 62B may be affixed directly to the faces of the facets. The bearing body 62A and 62B may be affixed by attachment means or screws. Alternatively, the side of the bearing body 62A and 62B that is to be in contact with the facet surface may be coated with tantalum or other bone growth inducing material. Such bone growth may help to provide for long term fixation of the facet implant 19B in the facet joint.

In another alternative embodiment illustrated in FIGS. 9-12, a facet implant 19C may be formed as a "V" shape. The facet implant 19C may be a single piece facet replacement structure and may include two fixation wings 28 and 30 and a connection means 32. The connection means 32 (or bridge) may be a length of a desired material between the fixation wings 28 and 30 that secures the fixation wings 28 and 30 at a desired angle relative to each other. The facet implant 19C fixation wings 28 and 30 may further include holes 33 for accepting an attachment member 25 or other fixation members. The facet implant 19C may form an included angle between the fixation wings 28 and 30. The shape of implant 19C may assist in attaching the implant 19C to the corresponding faces of a resected pair of facets.

The fixation wings 28 and 30 of facet implant 19C may be situated at a desired angle on either side of the connection means 32. The fixation wings 28 or 30 as illustrated form a substantially "V" shape with connection means 32 but may be affixed to the connection means 32 at any number of desired angles, from approximately 0° to 180°, or from straight to a very acute "V" shape. Such a facet implant 19C may be formed of the same polymers, elastomers, or other plastics as previously described for facet implant 19. In one embodiment, facet implant 19C may be made from coating or embedding softer materials over more rigid materials. For example, the facet implant 19C may be formed of stainless steel plates coated by polyurethane or nitrile rubber. Additionally, as previously described, tantalum metal, Trabecular™ metal or other bone in-growth materials can be affixed to the facet implant 19C so as to induce bone growth.

Facet implant 19C may be used as a partial or complete facet joint replacement. Facet implant 19C may also replace the function of the joint capsule, which may be partially, substantially, or completely removed during insertion of the facet implant 19C. The shape of the facet implant 19C may create a structure with more support and load bearing characteristics than facet implant 19. The shape of facet implant 19C may provide significant structural support between facets in a manner similar to an "L" bracket on the underside of a shelf.

Insertion of facet implant 19C may be substantially similar to insertion of facet implant 19 including resection of the facets some desired amount. In some embodiments the opposing facets may be resected. Afterwards, one fixation wing 28 may be attached to the resected surface of the superior vertebra and one fixation wing 30 may be attached to the resected surface of the inferior vertebra. The attachment angle of the fixation wings 28 and 30 may be selected depending on the materials used and the force desired.

Figure 13:
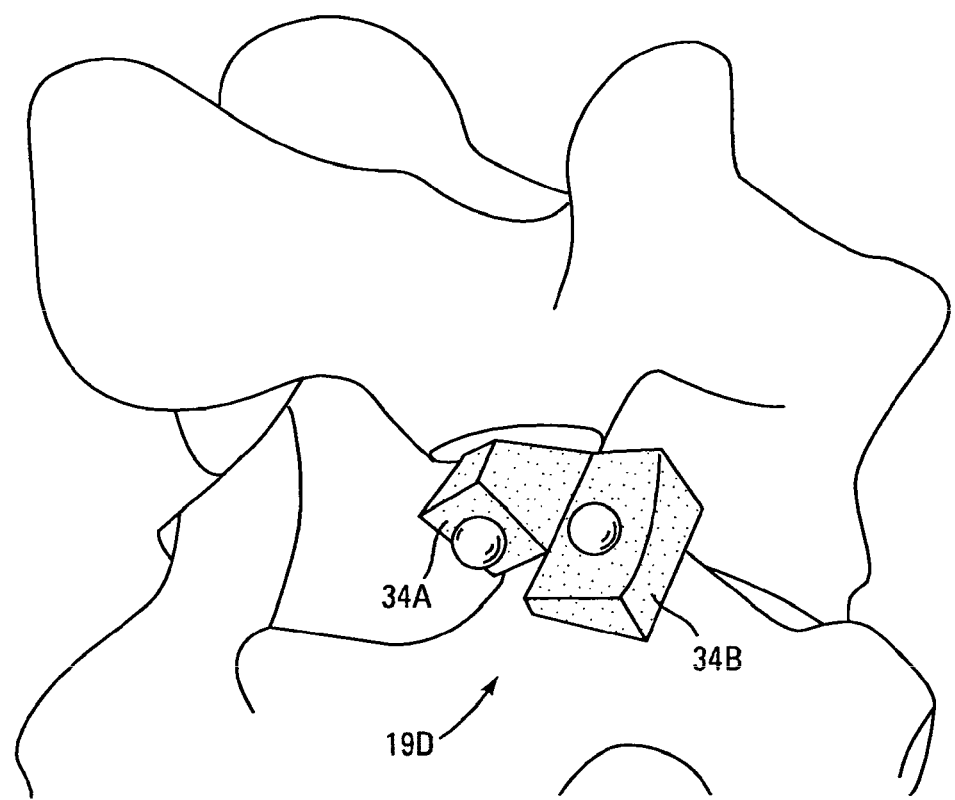
FIG. 13 illustrates another alternative embodiment of the facet implant of FIG. 4 inserted into the spine.
Figure 14:
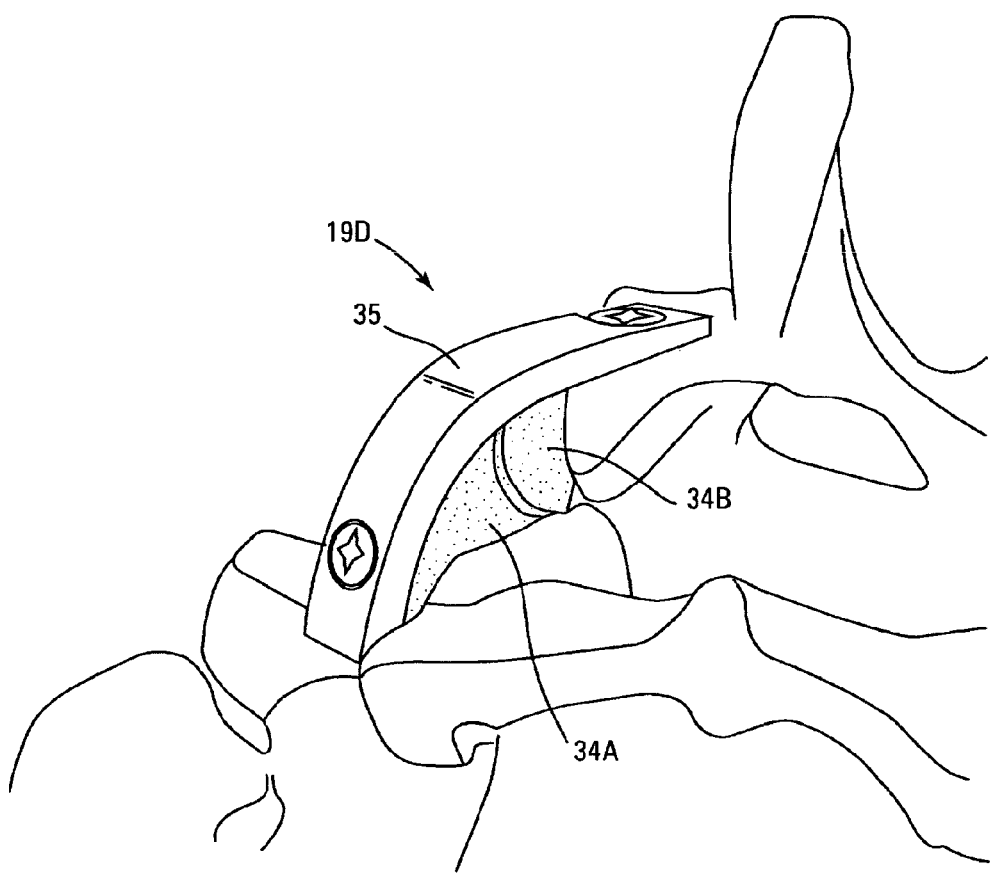
FIG. 14 illustrates an alternative embodiment of the facet implant of FIG. 13.
Figure 15:
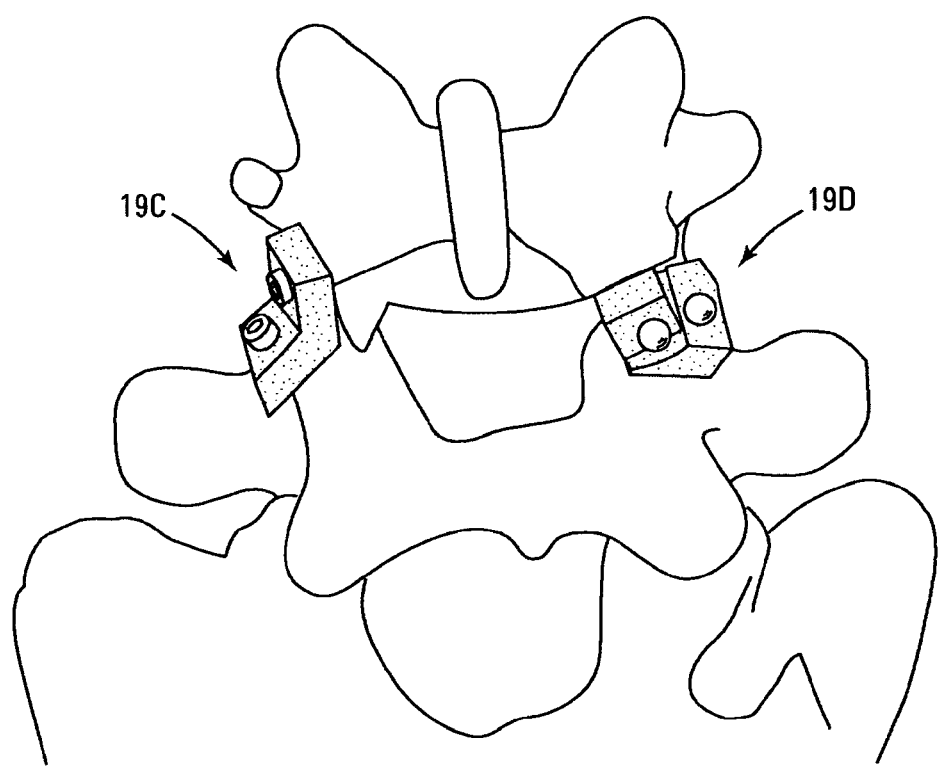
FIG. 15 illustrates the facet implant of FIG. 9 inserted on a first (left) facet joint and the facet implant of FIG. 13 inserted on a second (right) facet joint.

In yet another embodiment, illustrated in FIGS. 13-15, the facet implant 19D may include two separate facet blocks 34A and 34B that articulate relative to one another. One facet block 34A may be attached to the superior vertebra and one facet block 34B may be attached to the inferior vertebra. After the facet blocks 34A and 34B are attached to the vertebrae, a band 35 may be inserted over the facet joint and the two facet blocks 34A and 34B. (FIGS. 13 and 15 illustrate the placement and relative positions of the blocks 34A and 34B without the band 35.) The two facet blocks 34A and 34B provide the structural support and the band 35 may draw the facet joint together or into a desired position. The band 35 may restrain the joint motion a desired amount and may function to replace the joint capsule. The band 35 can be fixed to the pedicle on one side and the lamina on the other side. Fixation may be accomplished with any type of attachment members, screws, bone anchors, bone fasteners, anchor means, etc., known to those skilled in the art. In further embodiments, fixation of the blocks 34A and 34B and the band 35 to the vertebrae may be aided or accomplished solely by bone growth materials such as the bone in-growth material previously discussed.

In still further embodiments, the band 35 may be used without the facet blocks 34A and 34B for stabilizing the facet joints. In such an embodiment the band 35 may be placed over the facet joint without performing any invasion or resection of the facet joint itself. The band 35 may, in such an application, provide a restraining or compressing force in a substantially similar manner to the facet implant 19 when placed without the bearing body 20. The band 35 may be secured to any desired portion of the pedicle and lamina.

Figure 16:
FIG. 16 illustrates a friction member that can be utilized to secure a facet implant of the present invention to the spine.
Figure 17:
FIG. 17 illustrates an alternative embodiment of the friction member of FIG. 16.

As illustrated in FIGS. 16-17, one or more friction members 37 may also be incorporated onto any of the above facet implants ("facet implant" without a reference number refers generally to any of the embodiments of the facet implant 19 discussed in the present application). Friction members 37 may be spikes, cleats, nubs, etc. oriented to help secure the facet implant to the vertebrae and reduce movement of the facet implant after implantation (i.e., movement reducing means). The friction members 37 can be in various forms, sizes, and shapes and may be oriented in a variety of ways relative to the facet implants.

In one embodiment, friction members 37 may include sharp spikes as shown in FIG. 17. When the facet implant is secured into the bone, the spikes may engage the bone. Friction members 37 may also be inserted by driving the friction member 37 into the bone like a nail. In embodiments such as illustrated in FIG. 16, friction member 37 may include shafts or anchors that may not be designed to pierce the bone. A drill or other tool may be used to clear a hole or other depression into which the friction member 37 may be inserted. In another embodiment, friction member 37 may be secured to the bone utilizing an adhesive.

The facet implant may be utilized to treat a variety of spinal column disorders. One disorder that may be treated includes spondylolisthesis. In spondylolisthesis, a superior vertebra may "slide" over the top of an inferior vertebra in a back-to-front direction. This condition often results from a pars fracture or a degenerative weakening of the joint around the facet. The relative movement of the superior vertebra with the inferior vertebra may cause significant pain in the spinal column. Insertion of the facet implants may aid in securing the superior vertebra back into realignment. Different facet implants may be utilized depending on the amount of resection undertaken and the amount of support that needs to be inserted. For example, facet implant may be more useful in binding the existing facet structure together and providing the facet joint with the proper spacing and a new bearing body 20 and/or bearing surface 21. Furthermore, facet implant 19C may be advantageous when more of the facet is removed and the remaining bone needs more support. Finally facet implant 19D, in combination with band 35, may provide both support and binding of the facet joint. In addition, as illustrated in FIG. 15, two different types of facet implants may be utilized on two different facets between the same two vertebrae.

Figure 1:
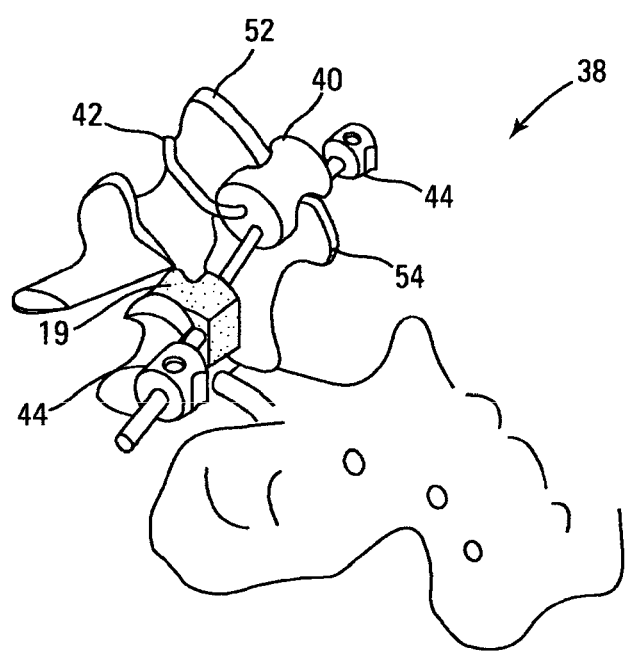
FIG. 1 illustrates one spinal stabilization system of the present invention that includes a spinous process spacer, facet spacers, and a connecting member connecting each.
Figure 2:
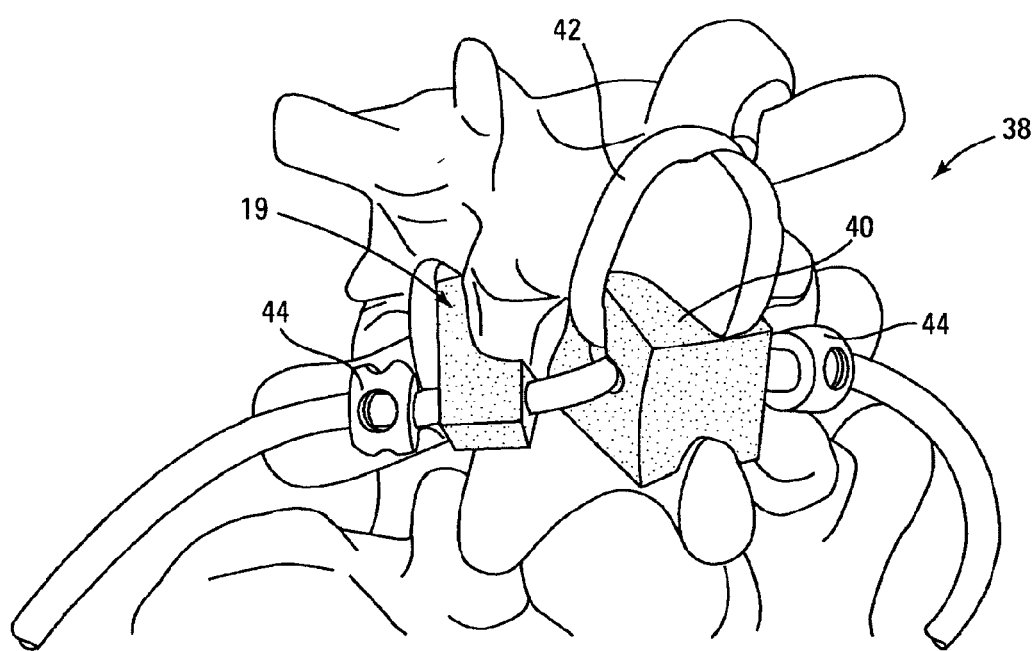
FIG. 2 illustrates one alternative embodiment of the spinal stabilization system of FIG. 1.
Figure 3:
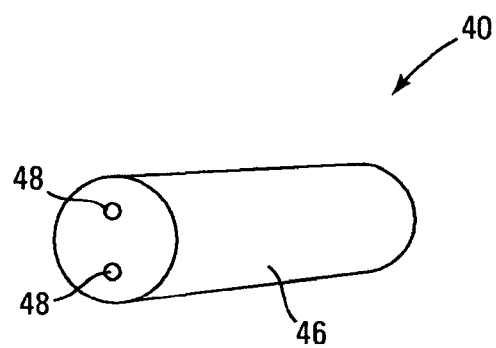
FIG. 3 is a perspective view of the spinous process spacer utilized in the spinal stabilization system of FIG. 1.

As illustrated in FIGS. 1-3, another aspect of the present invention may include incorporating the facet implant into a spinal stabilization system 38. (Any of the above facet implants 19A-D may be used in combination with system 38, but facet implant 19 will be utilized in the description of the present embodiment.) System 38 may include a spinous process spacer 40, one or more facet implants 19, a flexible connecting member 42 such as a cord, and one or more pedicle screws 44. The spinous process spacer 40 (i.e., spacing means) includes a body 46 with one or more passages 48 formed through the body 46. The passages 48 may be of a size and shape to receive the flexible connecting member 42. The facet implant 19 may be substantially the same as described above but may also include a passage 50 (see FIG. 4) to accommodate the flexible connecting member 42. Alternative facet implants 19C or 19D may also be used with system 38.

The spinous process spacer 40 may include a body 46 that is substantially cylindrical. However, as illustrated in FIG. 2, the body 46 may be different shapes, such as rectangular, triangular, or any other shape. Other shapes may include square, ball, octagonal, etc. Various different sizes and shapes of the body 46 may provide a different kind and amount of support to the spinous processes of the adjacent vertebrae.

As illustrated in FIG. 4, in one embodiment a passage 50 may be formed through the bearing body 20. In alternative embodiments, the passage 50 may be through any portion of the facet implant 19 that allows for the flexible connecting member 42 to pass through. Furthermore, depending on the placement of system 38, the passage 50 may be an indentation or channel on the surface of the facet implant 19 that receives the flexible connecting member. In still further embodiments the flexible connecting member 42 may not even be connected to a facet implant 19 or the facet implant 19 may not be incorporated into system 38, but may simply be used concurrently and independently for achieving the desired spinal stabilization.

The flexible connecting member 42 utilized to secure the spinous process spacer 40 with the other components of the system 38 (i.e., spacer securing means) is well known in the art and may be made of a multiple layer Dacron™ construction. Dacron™ is a polyester fiber that is obtained from ethylene glycol and terephthalic acid. Other suitable biocompatible materials may also be utilized. The pedicle screws 44 may be any type of anchor, bone anchor, or bone fastening means that can accommodate a flexible connecting member 42. One such screw is used in the Dynesys™ system described further at EP 0669109 B1 and WO 94/17745. Other systems may include Silhouette pedicle screws or any type of pedicle screw known to those skilled in the art and useful for securing the flexible connecting member 42 (i.e., flexible connecting member securing means).

The placement of system 38 may first involve the distraction of two successive spinous processes 52 and 54. The spinous process spacer 40 may then be inserted between the spinous processes 52 and 54. The spinous processes 52 and 54 may conform around the spinous process spacer 40 when the distraction force is relaxed. The facet implants 19 may then be implanted as previously described (or, alternatively, placed before the spinous process spacer 40). Facet implants 19 may be secured to one or both of the facet joints. The facet implants 19 should be inserted in such a position that the passage 50 can accommodate the flexible connecting member.

The flexible connecting member 42 may then be utilized to connect the spinous process spacer 40 with the facet implant 19 and the pedicle screws 44. As illustrated in the present embodiment, the flexible connecting member 42 may be threaded through a first pedicle screw 44, through a first facet implant 19, and through the spinous process spacer 40. The flexible connecting member 42 may then go around the first spinous process 52, through the spinous process spacer 40 again, and then through a second implant 19. The flexible connecting member 42 is then attached to a second pedicle screw 44. In alternative embodiments, the flexible connecting member 42 may also be wrapped around the second spinous process 54. The amount of tension placed on flexible connecting member 42 can be selected as desired depending on the "cinching" type force to be placed on the vertebrae.

The system 38 may accomplish a number of goals in combination with the facet implant 19. The system 38 may be utilized to reduce spondylolisthesis by securing the superior vertebra back into alignment with the inferior vertebra by utilizing the flexible connecting member 42 in combination with the other pieces of system 38. The system 38 may also be utilized to just prevent further sliding of the two vertebrae. Moreover, the system 38 may cause or induce some amount of lordosis of the spine, taking or relieving pressure on the anterior annulus, nucleus, and/or the posterior annular wall. Induced lordosis may also be caused by one or more of the other the embodiments discussed herein.

Various modifications and additions may be made to the exemplary structures and steps discussed. Various combinations, permutations, and rearrangements of those structures and steps may similarly be made without departing from the scope of the present invention. Accordingly, the scope of the present invention is intended to embrace all such alternatives, modifications, and variations as fall within the scope of the claims, together with all equivalents thereof.

What is claimed:

1. A method of stabilizing two adjacent vertebrae, comprising:

inserting a portion of a vertebral implant between a first facet of a first vertebra and a second facet of a second vertebra, the vertebral implant including polymeric material molded between a first piece of porous tantalum metal and a second piece of porous tantalum metal, a portion of the polymeric material being inserted between and in contact with the first facet and the second facet;

positioning the first piece of porous tantalum metal of the vertebral implant against a bony surface of the first vertebra that does not face the second facet; and positioning the second piece of porous tantalum metal of the vertebral implant against a bony surface of the second vertebra that does not face the first facet.

2. The method of claim 1, wherein the polymeric material penetrates into each of the first and second pieces of porous tantalum metal.

* * * * *